United States Patent

Bettarini et al.

[11] Patent Number: 5,916,847
[45] Date of Patent: Jun. 29, 1999

[54] ARYLHETEROCYCLES WITH HERBICIDAL ACTIVITY

[75] Inventors: Franco Bettarini; Piero La Porta, both of Novara; Giovanni Meazza, Saronno; Giampaolo Zanardi, Vigevano; Ernesto Signorini, Malnate; Domenico Portoso, Lodi, all of Italy

[73] Assignee: Isagro Ricerca S.r.l., Milan, Italy

[21] Appl. No.: 08/819,448

[22] Filed: Mar. 17, 1997

[30] Foreign Application Priority Data

Mar. 21, 1996 [IT] Italy ................................. MI96A0554
May 15, 1996 [IT] Italy ................................. MI96A0974

[51] Int. Cl.[6] .......................... A01N 33/06; C07D 209/38
[52] U.S. Cl. .......................... 504/285; 504/286; 548/513; 548/143; 548/128; 548/136; 548/262.4; 548/215; 548/356.1; 544/224
[58] Field of Search ............................ 548/513; 504/285, 504/286

[56] References Cited

U.S. PATENT DOCUMENTS 4,536,209  8/1985  Jikihara et al. ............................ 71/96
4,948,418  8/1990  Semple ...................................... 71/92

FOREIGN PATENT DOCUMENTS

| 0 068 822 | 1/1983 | European Pat. Off. . |
| 0 211 805 | 2/1987 | European Pat. Off. . |
| 0 468 930 A1 | 1/1992 | European Pat. Off. . |
| 44 24 791 A1 | 1/1986 | Germany . |
| 2 163 427 | 2/1986 | United Kingdom . |
| WO 94/05668 | 3/1994 | WIPO . |
| WO 95/06643 | 3/1995 | WIPO . |

*Primary Examiner*—Johann Richter
*Assistant Examiner*—Ebenezer Sackey
*Attorney, Agent, or Firm*—Oblon, Spivak, McClelland, Maier & Neustadt, P.C.

[57] ABSTRACT

Arylheterocycles having the general formula (I):

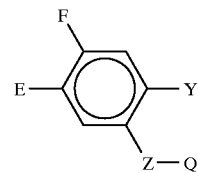

and process for preparing them. The arylheterocycles having the general formula (I) display high herbicidal activity.

20 Claims, No Drawings

ARYLHETEROCYCLES WITH HERBICIDAL ACTIVITY

The present invention relates to novel arylheterocycles.

More particularly, the present invention relates to arylheterocycles having high herbicidal activity, to a process for preparing them and to their use as herbicidal agents for controlling weeds in crops.

Arylheterocycles displaying herbicidal activity are disclosed in, among other references, U.S. Pat. Nos. 3,835,862; 4,431,822; 4,536,209; 4,736,068; 4,881,967 and 4,948,418. However, such products proved to be poorly selective because they are generally harmful also to most crops.

This present Applicant has found now new arylheterocycles which, besides displaying a high herbicidal activity against a large number of weeds, simultaneously display a low phytotoxicity for one or more from most interesting crops from the agricultural viewpoint and are consequently suitable for use as selective herbicides.

Therefore, the subject-matter of the present invention are arylheterocycles having the general formula (I):

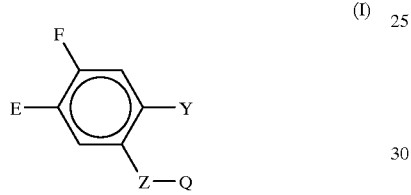

(I)

wherein:

Y represents a hydrogen atom; a chlorine, fluorine, or bromine atom; a linear or branched $C_1$–$C_4$ alkyl or haloalkyl radical, a linear or branched $C_1$–$C_4$ alkoxy or haloalkoxy; a linear or branched $C_1$–$C_4$ alkylthio or haloalkylthio;

Z represents an oxygen atom or a sulfur atom;

Q represents one of the following $Q_1$–$Q_7$ radicals (as represented by the following general formula):

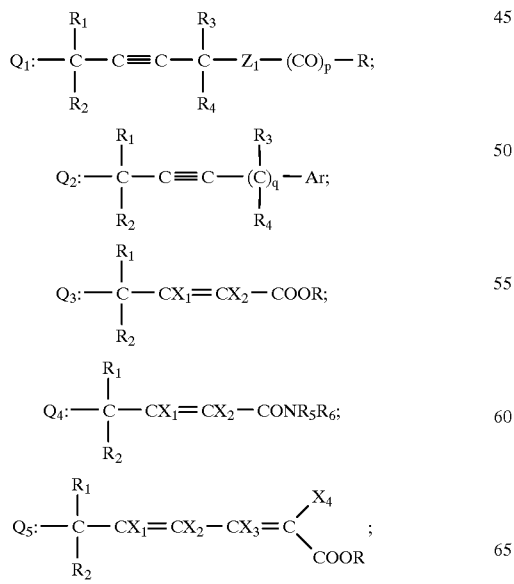

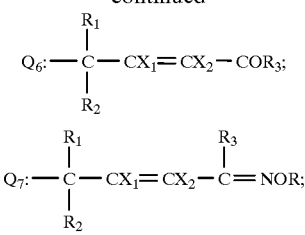

wherein:

R represents a hydrogen atom; a linear or branched $C_1$–$C_6$ alkyl or haloalkyl radical; a $C_3$–$C_6$ cycloalkyl radical; a $C_4$–$C_9$ cycloalkyl alkyl radical; a linear or branched $C_3$–$C_6$ cyanoalkyl radical; a linear or branched $C_3$–$C_6$ alkoxyalkyl radical; an oxoethanyl radical or a tetrahydrofuranyl radical, both possibly substituted with linear or branched $C_1$–$C_4$ alkyl radicals; a phenyl radical, a $C_7$–$C_9$ phenylalkyl radical or a pyridyl radical, with said radicals being possibly substituted with one or more halogen atoms as chlorine, fluorine, bromine, or iodine atoms, or with one or more radicals selected from linear or branched $C_1$–$C_4$ alkyl or haloalkyl radicals or from linear or branched $C_1$–$C_4$ alkoxy o haloalkoxy radicals;

$R_1$, $R_2$, $R_3$, and $R_4$ each independently, represent a hydrogen atom or a linear or branched $C_1$–$C_4$ alkyl or haloalkyl radical;

$R_5$ and $R_6$, each independently, represent a hydrogen atom; a linear or branched $C_1$–$C_4$ alkyl radical; or, together, they represent a $C_2$–$C_5$ alkylene chain, or a $C_2$–$C_5$ oxyalkylene chain;

Ar represents a phenyl radical or a pyridyl radical, with both of them being possibly substituted with one or more halogen atom as chlorine, fluorine, bromine or iodine atoms, or one or more radicals selected from linear or branched $C_1$–$C_4$ alkyl or haloalkyl radicals, or linear or branched $C_1$–$C_4$ alkoxy or haloalkoxy radicals;

$X_1$, $X_2$, $X_3$ and $X_4$, each independently, represent a hydrogen atom; a halogen atom as a chlorine, fluorine, bromine or iodine atom; a linear or branched $C_1$–$C_4$ alkyl or haloalkyl; a linear or branched $C_1$–$C_4$ alkoxy or haloalkoxy radical;

$Z_1$ represents an oxygen atom or a sulfur atom;

p represents 0 or 1;

q represents 0 or 1;

E represents one from the following heterocyclic radicals represented by the following $E_1$–$E_8$ general formulae:

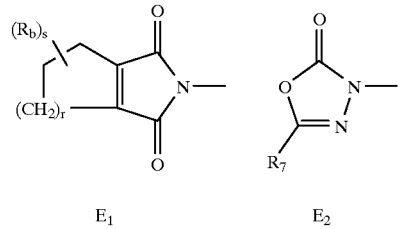

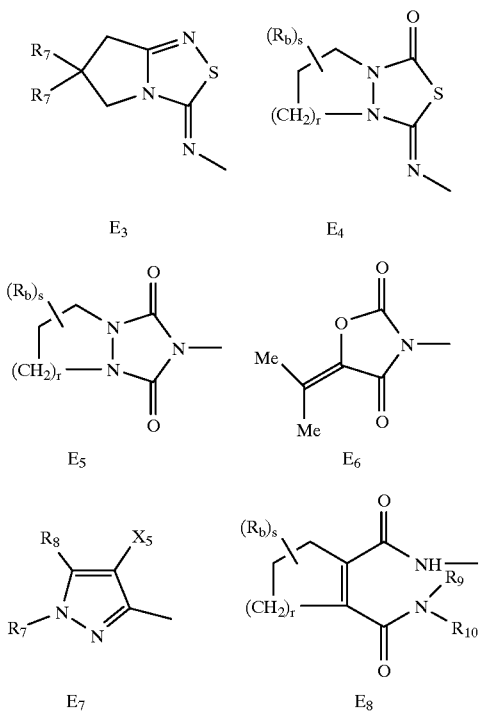

wherein:

$R_b$ represents a linear or branched $C_1$–$C_3$ alkyl radical;

$R_7$ represents a linear or branched $C_1$–$C_6$ alkyl or haloalkyl radical;

$R_8$ represents a hydrogen atom; a linear or branched $C_1$–$C_6$ alkoxy or haloalkoxy radical; a linear or branched $C_1$–$C_6$ alkylthio or haloalkylthio radical;

$R_9$ and $R_{10}$, each independently, represent a hydrogen atom, a linear or branched $C_1$–$C_6$ alkyl radical; or, together, they represent a $C_2$–$C_5$ alkylene or oxyalkylene chain;

$X_5$ represents a hydrogen atom; or a halogen atom as a chlorine, fluorine, bromine or iodine atom;

r represents 1 or 2;

s represents an integer having a value comprised within the range of from 0 and 2 inclusive.

The arylheterocycles having the general formula (I) display a high herbicidal activity.

Specific examples of arylheterocycles having the general formula (I) which deserve interest owing to their herbicidal activity are:

N-[4-chloro-2-fluoro-5-(4-methoxybut-2-ynyloxy)phenyl]cyclohex-1-ene-1,2-dicarboximide;

methyl 4-[2-chloro-5-(cyclohex-1-ene-1,2-dicarboximido)-4-fluorophenoxy]crotonate;

methyl 4-[2-chloro-5-(cyclohex-1-ene-1,2-dicarboximido)-4-fluorophenoxy]-3-methoxybut-(E)-2-enoate;

N-[4-chloro-2-fluoro-5-(4-ethoxybut-2-ynyloxy)phenyl]cyclohex-1-ene-1,2-dicarboximide;

N-[4-chloro-2-fluoro-5-(4-propoxybut-2-ynyloxy)phenyl]cyclohex-1-ene-1,2-dicarboximide;

N-[4-chloro-2-fluoro-5-(4-isopropoxybut-2-ynyloxy)phenyl]cyclohex-1-ene-1,2-dicarboximide;

N-[4-chloro-2-fluoro-5-(5-methoxypent-3-yn-2-yloxy)phenyl]-cyclohex-1-ene-1,2-dicarboximide;

N-[4-chloro-2-fluoro-5-(5-ethoxypent-3-yn-2-yloxy)phenyl]-cyclohex-1-ene-1,2-dicarboximide;

N-[4-chloro-2-fluoro-5-(5-isopropoxypent-3-yn-2-yloxy)phenyl]-cyclohex-1-ene-1,2-dicarboximide;

N-[4-chloro-2-fluoro-5-(4-methoxypent-2-ynyloxy)phenyl]-cyclohex-1-ene-1,2-dicarboximide;

N-[4-chloro-2-fluoro-5-(4-difluoromethoxybut-2-ynyloxy)phenyl]-cyclohex-1-ene-1,2-dicarboximide;

N-[4-chloro-2-fluoro-5-(4-(1,1,2,2-tetrafluoroethoxy)but-2-ynyloxy)phenyl]cyclohex-1-ene-1,2-dicarboximide;

N-[4-chloro-2-fluoro-5-(5-(methoxyethoxy)pent-3-yn-2-yloxy)phenyl]cyclohex-1-ene-1,2-dicarboximide;

N-[4-chloro-2-fluoro-5-(4-(cyanomethoxy)but-2-ynyloxy)phenyl]cyclohex-1-ene-1,2-dicarboximide;

N-[4-chloro-2-fluoro-5-(5-pyrid-2-yloxypent-3-yn-2-yloxy)phenyl]cyclohex-1-ene-1,2-dicarboximide;

N-[4-chloro-2-fluoro-5-(3-phenylprop-2-ynyloxy)phenyl]cyclohex-1-ene-1,2-dicarboximide;

ethyl 4-[2-chloro-5-(cyclohex-1-ene-1,2-dicarboximido)-4-fluorophenoxy]crotonate;

2,2,2-trifluoroethyl 4-[2-chloro-5-(cyclohex-1-ene-1,2-dicarboximido)-4-fluorophenoxy]crotonate;

propyl 4-[2-chloro-5-(cyclohex-1-ene-1,2-dicarboximido)-4-fluorophenoxy]crotonate;

butyl 4-[2-chloro-5-(cyclohex-1-ene-1,2-dicarboximido)-4-fluorophenoxy]crotonate;

methyl 4-[2-chloro-5-(cyclohex-1-ene-1,2-dicarboximido)-4-fluorophenoxy]pent-2-enoate;

ethyl 4-[2-chloro-5-(cyclohex-1-ene-1,2-dicarboximido)-4-fluorophenoxy]pent-2-enoate;

2,2,2-trifluoroethyl 4-[2-chloro-5-(cyclohex-1-ene-1,2-dicarboximido)-4-fluorophenoxy]pent-2-enoate;

propyl 4-[2-chloro-5-(cyclohex-1-ene-1,2-dicarboximido)-4-fluorophenoxy]pent-2-enoate;

isopropyl 4-[2-chloro-5-(cyclohex-1-ene-1,2-dicarboximido)-4-fluorophenoxy]pent-2-enoate;

butyl 4-[2-chloro-5-(cyclohex-1-ene-1,2-dicarboximido)-4-fluorophenoxy]pent-2-enoate;

ethyl 4-[2-chloro-5-(cyclohex-1-ene-1,2-dicarboximido)-4-fluorophenoxy]-3-ethoxybut-(E)-2-enoate;

methyl 4-[2-chloro-5-(cyclohex-1-ene-1,2-dicarboximido)-4-fluorophenoxy]-2-methylpent-2-enoate;

methoxyethyl 4-[2-chloro-5-(cyclohex-1-ene-1,2-dicarboximido)-4-fluorophenoxy]crotonate;

methoxyethyl 4-[2-chloro-5-(cyclohex-1-ene-1,2-dicarboximido)-4-fluorophenoxy]pent-2-enoate;

methyl 6-[2-chloro-5-(cyclohex-1-ene-1,2-dicarboximido)-4-fluorophenoxy]sorbate;

N,N-dimethyl 4-[2-chloro-5-(cyclohex-1-ene-1,2-dicarboximido)-4-fluorophenoxy]pent-2-enamide;

N,N-tetramethylene 4-[2-chloro-5-(cyclohex-1-ene-1,2-dicarboximido)-4-fluorophenoxy]pent-2-enamide;

N-[4-chloro-2-fluoro-5-(4-hydroxybut-2-ynyloxy)phenyl]cyclohex-1-ene-1,2-dicarboximide;

N-[4-chloro-2-fluoro-5-(4-acetyloxybut-2-ynyloxy)phenyl]cyclohex-1-ene-1,2-dicarboximide.

A further subject-matter of the present invention are the processes for preparing the compounds having the general formula (I).

The compounds having the general formula (I), in which Z represents an oxygen atom or a sulfur atom, can be obtained by means of a process comprising reacting a phenol or a thiophenol having the general formula (II):

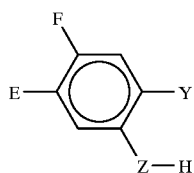

(II)

in which Z, Y and E have the same meaning as disclosed above, with a compound having the general formula (III):

X'—Q  (III)

in which Q has the same meanings as disclosed above and X' represents a halogen atom, preferably chlorine and bromine, or an R'SO$_2$O moiety in which R' represents a linear or branched C$_1$–C$_4$ alkyl or haloalkyl radical, or a phenyl radical, which may also be possibly substituted by linear or branched C$_1$–C$_3$ alkyl radicals, nitro groups, halogen atoms as chlorine, fluorine, or bromine.

The above process can be advantageously carried out in the presence of an inert organic solvent and in the presence of an either inorganic or organic base, at a temperature comprised within the range of from −10° C. to the boiling temperature of the solvent used, preferably comprised within the range of from 0° C. to 100° C.

Inert organic solvents useful for the intended purpose are, for example, benzene, toluene, xylene, acetone, methyl ethyl ketone, methyl propyl ketone, ethyl acetate, dimethoxyethane, diisopropyl ether, tetrahydrofuran, dioxane, acetonitrile, N,N-dimethylformamide, N,N-dimethylacetamide, N-methyl pyrrolidone, dimethylsulfoxide.

Inorganic bases useful for the intended purpose are, for example, sodium, potassium and calcium hydroxides and carbonates.

Useful organic bases are, for example, triethylamine, pyridine, 4-dimethylamino pyridine, diazabicyclooctane (DABCO), diazabicycloundecene (DBU).

The above process can also be advantageously carried out in a two-phase system under phase transfer conditions as described, for example, by Dehmlow and Dehmlow in "Phase Transfer Catalysis" (1983), Verlag Chemie Publisher.

The phenols or thiophenols having the general formula (II) and the compounds having the general formula (III), are available on the market or they can be easily prepared according to known methods of organic chemistry.

The compounds having the general formula (I) in which E represents the E$_1$ moiety having the general formula (I-1):

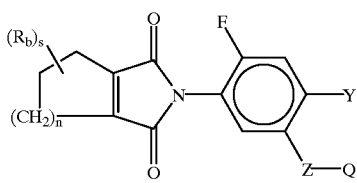

(I-1)

in which Y, Z, Q, R$_b$, s and r have the meanings disclosed above can be prepared, according to an alternative process, by reacting an anhydride having the general formula (IV):

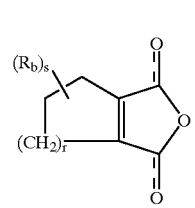

(IV)

wherein R$_b$, s, and r have the same meanings as disclosed above, with an aniline having the general formula (V):

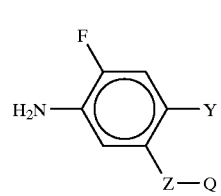

(V)

wherein Y, Z, and Q have the same meanings as defined above. The above reaction can be carried out either in the absence or in the presence of a inert organic solvent, at a temperature comprised within the range of from room temperature up to the boiling temperature of the possibly used solvent, preferably of from 60° C. to 200° C., possibly in the presence of a catalyst.

Inert organic solvents useful for this purpose are, for example, benzene, toluene, xylene, chlorobenzene, acetic acid, diisopropyl ether, dimethoxyethane, tetrahydrofuran, dioxane.

Useful catalyst for that purpose are for example, mixtures of nitrogenous organic bases such as, e.g., triethylamine, piperidine, pyrrolidine with aliphatic carboxy acids such as, e.g., acetic acid, propionic acid, butyric acid.

In order to facilitate the above reaction, water formed during the condensation reaction can be suitably removed by azeotropic distillation.

The anhydrides having the general formula (IV) and the anilines having the general formula (V) can be easily prepared according to known methods of organic chemistry.

The compounds having the general formula (I) in which E represents the E$_4$ moiety having the general formula (I-4):

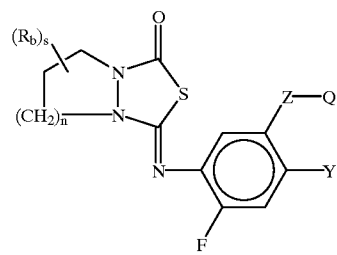

(I-4)

in which Y, Z, Q, R$_b$, s and r have the above disclosed meanings, can be alternatively prepared by reacting phosgene or trichloromethyl chloroformate, and a compound having general formula (VI):

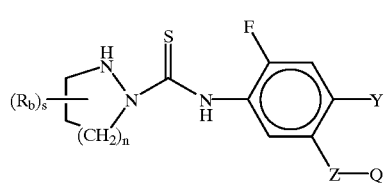
(VI)

wherein Y, Z, Q, $R_b$, s and r have the meaning disclosed above.

The reaction is carried out by reacting the compounds having the general formula (VI), either dissolved or suspended in a suitable inert organic solvent, with phosgene or trichloromethyl chloroformate, possibly also dissolved in a suitable inert organic solvent, at the temperature comprised within the ranae of from 20° C. up to the boiling temperature of the reaction mixture and possibly in the presence of an inorganic or organic base.

Useful inert organic solvents for that purpose are, for example, methylene chloride, chloroform, 1,2-dichloroethane, benzene, toluene, xylene, chlorobenzene, diethyl ether, tetrahydrofuran, dioxane, ethyl acetate.

Useful bases for that purpose are inorganic bases such as, for example, sodium bicarbonate, sodium carbonate, potassium carbonate, or organic bases, such as, e.g., triethylamine, pyridine, 4-dimethylaminopyridine, and so forth.

In their turn, the compounds having the general formula (VI) can be prepared by reacting an aryl isothiocyanate of formula (VII):

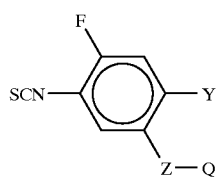
(VII)

in which Y, Z, and Q have the meanings as disclosed above, with a compound having general formula (VIII):

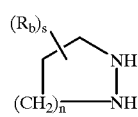
(VIII)

wherein $R_b$, s and r have the same meanings as disclosed above.

The aryl isothiocyanates having formula (VII) can be prepared by reacting the corresponding anilines of general formula (V), with thiophosgene.

The compounds having general formula (VIII) are known from the literature.

The compounds having the general formula (I) in which E represents the $E_5$ moiety having the general formula (I-5):

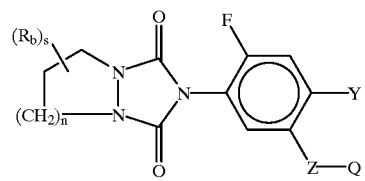
(I-5)

in which Y, Z, Q, $R_b$, s and r have the same meanings as disclose above, can be alternatively prepared by reacting with phosgene or trichloromethyl chloroformate, a compound having general formula (IX):

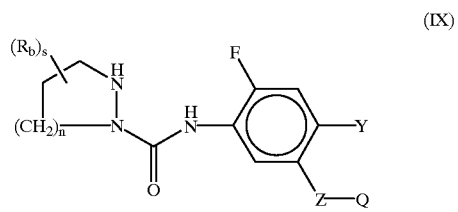
(IX)

wherein Y, Z, Q, $R_b$, s and r have the meanings disclosed above.

The reaction is carried out by reacting the compounds having the general formula (IX), either dissolved or suspended in a suitable inert organic solvent, with phosgene or trichloromethyl chloroformate, possibly also dissolved in a suitable inert organic solvent, at the temperature comprised within the range of from 20° C. up to the boiling temperature of the reaction mixture and possibly in the presence of an inorganic or organic base.

Useful inert organic solvents for that purpose are, for example, methylene chloride, chloroform, 1,2-dichloroethane, benzene, toluene, xylene, chlorobenzene, ethyl ether, tetrahydrofuran, dioxane, ethyl acetate.

Useful bases for that purpose are inorganic bases such as, e.g., sodium bicarbonate, sodium carbonate, potassium carbonate, or organic bases, such as, e.g., triethylamine, pyridine, 4-dimethylamino pyridine, and so forth.

The compounds having the general formula (IX) can be prepared in their turn by reacting an aryl isocyanate having the general formula (X) with a compound having the general formula (VIII).

The aryl isocyanates having formula (X) can be prepared by starting from anilines of formula (V) by reaction with phosgene or trichloromethyl chloroformate.

The compounds having the general formula (I) in which E represents the $E_7$ moiety having the general formula (I-7):

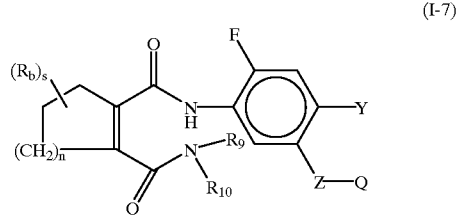
(I-7)

in which Y, Z, Q, $R_9$, $R_{10}$, $R_b$, s and r have the meanings disclosed above, can be alternatively prepared by reacting a compound having the general formula (I-1) with an amine of general formula (X):

wherein $R_9$ and $R_{10}$ have the meanings disclosed above.

The reaction can be carried out in an organic solvent, at a temperature comprised within the range of from 0° C. up to the boiling temperature of the solvent used, possibly in the presence of a base as catalyst.

Examples of suitable organic solvents for that purpose are methylene chloride, chloroform, carbon tetrachloride, chlorobenzene, benzene, toluene, xylene, hexane, octane, cyclohexane, ethyl ether, dioxane, tetrahydrofuran, dimethoxyethane, acetone, methyl ethyl ketone, acetonitrile, ethyl acetate, dimethylformamide.

Examples of suitable bases are triethylamine, pyridine, potassium carbonate, sodium carbonate.

The amines having the general formula (X) are known products.

In same cases, the compounds having the general formula (I) can be obtained as two or more optical and/or geometric isomers.

Therefore, it falls within the spirit of the present invention taking into consideration both compounds having the general formula (I) which are isomerically pure, and mixture thereof, possibly obtained during the preparation of the compounds having the general formula (I), or deriving from an incomplete separation of said isomers, in any proportions.

The compounds having the general formula (I) according to the present invention displayed a high herbicidal activity which makes them suitable for use in agricultural field for protecting crops from weeds.

In particular, the compounds having the general formula (I) are effective for controlling, both pre-emergency and post-emergency, a large number of monocotyledonous and dicotyledonous weeds. Said compounds display simultaneously compatibility or absence or toxic effects towards useful crops, both in pre-emergency and post-emergency treatments.

Examples of weeds which can be effectively controlled by using the compounds having the general formula (I) of this present invention are: *Sorghum halepense, Echinocloa crusgalli, Avena fatua, Amni maius, Abutilon theofrasti, Stellaria media, Convolvulus sepium, Amaranthus retroflexus, Chenopodium album, Galium aparine, Senecio vulgaris, Alopecurus myosuroides, Cyperus spp.*, and so forth.

At the application doses useful for agrarian application, the above compounds did not display toxic effects towards important crops, as rice (*Oryza sativa*), wheat(Triticum spp.), corn (*Zea mais*), soy bean (*Glycine max*), and so forth.

A further object of this present invention is a method for controlling weeds in cultivated areas, by means of the application of the compounds having the general formula (I).

The amount of compound to be applied in order to achieve the desired effect can vary as a function of several factors, such as, e.g., the used compound, the crop to be protected, the weed to be killed, the infestation level, the weather conditions, the characteristics of soil, the application method, and so forth.

Compound doses comprised between the range of from 1 g to 1000 g per hectare generally allow a sufficient control to be obtained.

For practical uses in agriculture, it is often advantageous using composition displaying herbicidal activity containing, as their active substance, one or more compounds having general formula (I), possibly also as a mixture of isomers.

Compositions can be used which are in the forms of dry powders, wettable powders, emulsifiable concentrates, microemulsions, pastes, pellets, solutions, suspensions, and so forth; the choice of the type of composition will depend on the specific use envisaged.

The compositions are prepared according to known methods, for example by diluting or dissolving the active substances with a solvent means and/or a solid extender, possibly in the presence of surfactants.

As inert solid extenders or carriers, China clay, alumina, silica, talc, bentonite, plaster, quartz, dolomite, actalpulgite, montmorillonite, diatomaceous earth, cellulose, starch, and so forth, can be used.

As inert liquid extenders, or diluents, of course besides water, organic solvent can be used, as aromatic hydrocarbons (xylenes, mixtures of alkylbenzenes, and so forth), aliphatic hydrocarbons (hexane, cyclohexane, and so forth), halogenated aromatic hydrocarbons (chlorobenzene, and so forth), alcohols (methanol, propanol, butanol, octanol, and so forth), esters (isobutyl acetate, and so forth), ketones (acetone, cyclohexanone, acetophenone, isophorone, ethyl amyl ketone, and so forth), or vegetable or mineral oils, or mixture thereof, and so forth.

As surfactants, there can be used wetting agents and emulsifiers of nonionic (polyethoxylated alkyl phenols, polyethoxylated fatty alcohols and so forth), anionic (alkylbenzene sulfonates, and alkylsulfonates, and so forth), cationic types (quaternary alkylammonium salts, and so forth).

Furthermore, dispersants (for example, lignin and its salts, cellulose derivatives, alginates, and so forth), stabilisers (for example, antioxidants, UV absorbers, and so forth) can be added.

In other to extend the range of action of the above said compositions, still other active is ingredients can be added to them such as, e.g., other herbicides, fungicides, insecticides or acaricides, as well as fertilisers.

The active substance concentration in the above said compositions can vary within a wide range, according to the active compound, the applications they are intended for, the environmental conditions and the type of formulation adopted.

In general, the active substance concentration in comprised within the range of from 1% to 90%, preferably of from 5% to 50%.

The examples reported in the following are supplied for the purpose of illustrating the present invention without limiting it.

EXAMPLE 1

Preparation of N-[4-chloro-2-fluoro-5-(4-methoxy-but-2-ynyloxy)phenyl]cyclohex-1-ene-1,2-dicarboximide (Compound No. 1)

To a solution of 1 g (3.38 mmol) of N-(4-chloro-2-fluoro-5-hydroxyphenyl)cyclohex-1-ene-1,2-dicarboximide in 10 ml of N,N-dimethylformamide, 470 mg (3.39 mmol) of potassium carbonate is added. The reaction mixture is kept under stirring, at room temperature, during 30 minutes.

Thereafter, a solution of 630 mg (3.54 mmol) of 4-methoxy-2-butynyl methanesulfonate in 5 ml of N,N-dimethylformamide is added dropwise and the mixture is heated at 60° C. for 4 hours.

The resulting mixture is poured into water (150 ml) and is then extracted with ethyl ether (3×50 ml).

The organic phase is washed until neutral with a saturated solution of sodium chloride, then is thoroughly dried with sodium sulfate and is concentrated on rotary evaporator.

The so obtained raw material is purified by chromatography on silica gel, eluting with 65:35 hexane:ethyl acetate.

A yield of 600 mg of a solid material with melting point 52–55° C., corresponding to Compound No. 1, is obtained.

EXAMPLE 2

Preparation of methyl 4-[2-chloro-5-(cyclohex-1-ene-1,2-dicarboximido)-4-fluorophenoxy]crotonate (Compound No.2)

An amount of 470 mg (3.39 mmol) of potassium carbonate is added to a solution of 1 g (3,38 mmol) of 2-chloro-5-(cyclohex-1-ene-1,2-dicarboximido)-4-fluorophenol in 10 ml of N,N-dimethylformamide. The reaction mixture is kept under stirring, at room temperature, during 30 minutes.

Then, a solution of 610 mg (3.41 mmol) of methyl bromocrotonate in 5 ml of N,N-dimethyl formamide is added dropwise, and the resulting mixture is heated at 60° C. during 4 hours.

The resulting mixture is poured into water (150 ml) and extracted with ethyl ether (3×50 ml). The organic phase is washed until neutral with a saturated solution of sodium chloride, then is dried over sodium sulfate and concentrated on a rotary evaporator.

The resulting raw material is purified by silica gel chromatography, eluting with 65:35 exane:ethyl acetate.

A yield of 520 mg is obtained of a white solid, corresponding to Compound No. 2, with melting point of 111° C.–112° C.

EXAMPLE 3

Preparation of methyl 4-[2-chloro-5-(cyclohex-1-ene-1,2-dicarboximido)-4-fluorophenoxy]-3-methoxybut-(E)-2-enoate (Compound No. 3)

A mixture consisting of 3.9 g (13.5 mmol) of methyl 4-(5-amino-2-chloro-4-fluorophenoxy)-3-methoxybut-(E)-2-enoate, 2.14 g (14 mmol) of 3,4,5,6-tetrahydrophthalic anhydride, 0.12 ml (1.2 mmol) of piperidine and 0.14 ml (2.4 mmol) of acetic acid in 30 ml of toluene, is heated at 90° C. during 8 hours.

After cooling, the above reaction mixture is washed, in the order, with water, a solution of 1% sodium carbonate in water, 1% hydrochloric acid in water and finally, with a saturated sodium chloride solution. The organic phase is dried with sodium sulfate and the solvent is evaporated off. The resulting raw material is purified by silica gel chromatography, eluting with a 65:35 exane:ethyl acetate mixture.

A yield of 5 g is obtained of a white solid corresponding to Compound No. 3, with melting point of 110° C.–112° C.

By operating in a similar way to as disclosed in Examples 1 and 2, starting from 2-chloro-5-(cyclohex-1-ene-1,2-dicarboximido)-4-fluorophenol and suitable halides or mesylates, or by operating in a similar way to as disclosed in Example 3, starting from 3,4,5,6-tetrahydrophthalic anhydride and suitably substituted anilines, the following compounds were obtained:

N-[4-chloro-2-fluoro-5-(4-ethoxybut-2-ynyloxy)phenyl] cyclohex-1-ene-1,2-dicarboximide (Compound No.4): solid with melting point 63–65° C.

N-[4-chloro-2-fluoro-5-(4-propoxybut-2-ynyloxy)phenyl] cyclohex-1-ene-1,2-dicarboximido (Compound No.5): solid with melting point 74–76° C.

N-[4-chloro-2-fluoro-5-(4-isopropoxybut-2-ynyloxy) phenyl]cyclohex-1-ene-1,2-dicarboximide (Compound No.6): a solid with melting point 111–113° C.

N-[4-chloro-2-fluoro-5-(5-methoxypent-3-yn-2-yloxy) phenyl]cyclohex-1-ene-1,2-dicarboximide (Compound No.7): a thick oil N-[4-chloro-2-fluoro-5-(5-ethoxypent-3-yn-2-yloxy) phenyl]cyclohex-1-ene-1,2-dicarboximide (Compound No.8): a thick oil N-[4-chloro-2-fluoro-5-(5-isopropoxypent-3-yn-2-yloxy) phenyl]cyclohex-1-ene-1,2-dicarboximide (Compound No.9): a thick oil N-[4-chloro-2-fluoro-5-(4-methoxypent-2-yn-yloxy) phenyl]cyclohex-1-ene-1,2-dicarboximide (Compound No.10): a thick oil N-[4-chloro-2-fluoro-5-(4-difluoromethoxybut-2-ynyloxy) phenyl]cyclohex-1-ene-1,2-dicarboximide (Compound No.11): a thick oil N-[4-chloro-2-fluoro-5-(4-(1,1,2,2-tetrafluorohethoxy)but-2-ynyloxy)phenyl]cyclohex-1-ene-1,2-dicarboximide (Compound No.12): a thick oil N-[4-chloro-2-fluoro-5-(5-(methoxyethoxy)pent-3-yn-2-yloxy)phenyl]cyclohex-1-ene-1,2-dicarboximide (Compound No.13): a thick oil N-[4-chloro-2-fluoro-5-(4-(cyanomethoxy)but-2-ynyloxy) phenyl]cyclohex-1-ene-1,2-dicarboximide (Compound No.14): a thick oil N-[4-chloro-2-fluoro-5-(5-pyrid-2-yloxypent-3-yn-2-yloxy) phenyl]cyclohex-1-ene-1,2-dicarboximide (Compound No.15): a thick oil N-[4-chloro-2-fluoro-5-(3-phenylprop-2-ynyloxy)phenyl] cyclohex-1-ene-1,2-dicarboximide (Compound No.16): a solid with melting point 120–122° C.

ethyl 4-[2-chloro-5-(cyclohex-1-ene-1,2-dicarboximido)-4-fluorophenoxy]crotonate (Compound No.17): a solid with m.p. 93–95° C.;

2,2,2-trifluoroethyl 4-[2-chloro-5-(cyclohex-1-ene-1,2-dicarboximido)-4-fluorophenoxy]crotonate (Compound No.18): a solid with m.p. 134–136° C.;

propyl 4-[2-chioro-5-(cyclohex-1-ene-1,2-dicarboximido)-4-fluorophenoxy]crotonate (Compound No.19): a solid material;

butyl 4-[2-chloro-5-(cyclohex-1-ene-1,2-dicarboximido)-4-fluorophenoxy]crotonate (Compound No.20): a thick oil;

methyl 4-[2-chloro-5-(cyclohex-1-ene-1,2-dicarboximido)-4-fluorophenoxy]pent-2-enoate (Compound No.21): a solid with m.p. 108–110° C.;

ethyl 4-[2-chloro-5-(cyclohex-1-ene-1,2-dicarboximido)-4-fluorophenoxy]pent-2-enoate (Compound No.22): a solid with m.p. 75–76° C.;

2,2,2-trifluoroethyl 4-[2-chloro-5-(cyclohex-1-ene-1,2-dicarboximido)-4-fluorophenoxy]pent-2-enoate (Compound No.23)

propyl 4-[2-chloro-5-(cyclohex-1-ene-1,2-dicarboximido)-4-fluorophenoxy]pent-2-enoate (Compound No.24): a thick oil;

isopropyl 4-[2-chloro-5-(cyclohex-1-ene-1,2-dicarboximido)-4-fluorophenoxy]pent-2-enoate (Compound No.25): a thick oil;

butyl 4-[2-chloro-5-(cyclohex-1-ene-1,2-dicarboximido)-4-fluorophenoxy]pent-2-enoate (Compound No.26): a thick oil;

ethyl 4-[2-chloro-5-(cyclohex-1-ene-1,2-dicarboximido)-4-fluorophenoxy]-3-ethoxybut-(E)-2-enoate (Compound No.27): a solid with m.p.79–81° C.;

methyl 4-[2-chloro-5-(cyclohex-1-ene-1,2-dicarboximido)-4-fluorophenoxy]-2-methyl-pent-2-enoate (Compound No.28): a solid with m.p.85–87° C.;

methoxyethyl 4-[2-chloro-5-(cyclohex-1-ene-1,2-dicarboximido)-4-fluorophenoxy]crotonate (Compound No.29): a solid with m.p. 85–87° C.;

methoxyethyl 4-[2-chloro-5-(cyclohex-1-ene-1,2-dicarboximido)-4-fluorophenoxy]pent-2-enoate (Compound No.30);

methyl 6-[2-chloro-5-(cyclohex-1-ene-1,2-dicarboximido)-4-fluorophenoxy]sorbate (Compound No.31): a solid with m.p. 137–139° C.;

N,N-dimethyl 4-[2-chloro-5-(cyclohex-1-ene-1,2-dicarboximido)-4-fluorophenoxy]pent-2-enamide (Compound No.32): a solid with m.p. 144–146° C.;

N,N-tetramethylene 4-[2-chloro-5-(cyclohex-1-ene-1,2-dicarboximido)-4-fluorophenoxy]pent-2-enamide (Compound No.33): a solid with m.p. 125–127° C.;

N-[4-chloro-2-fluoro-5-(4-hydroxybut-2-ynyloxy)phenyl] cyclohex-1-ene-1,2-dicarboximide(Compound No.34): a solid;

N-[4-chloro-2-fluoro-5-(4-acetyloxybut-2-ynyloxy) phenyl] cyclohex-1-ene-1,2-dicarboximide (Compound No.35): a solid.

EXAMPLE 5

By operating in a similar way to what disclosed in Examples 1 and 2 the following compounds were obtained by alkylating 5-heterocyclyl-2-chloro-4-fluorophenols with the corresponding halides or mesylates:

methyl 4-[5-(5-tert-butyl-1,3,4-oxadiazol-2(3H)-on-3-yl)-2-chloro-4-fluorophenoxy]-3-methoxybut-(E)-2-enoate (Compound No.36): a solid with m.p. 84–85° C.

methyl 4-[5-(5-tert-butyl-1,3,4-oxadiazol-2(3H)-on-3-yl)-2-chloro-4-fluorophenoxy]pent-2-enoate(Compound No.37): a solid with m.p. 89–91° C.

methyl 4-[5-(5-isopropyl-1,3,4-oxadiazol-2(3H)-on-3-yl)-2-chloro-4-fluorophenoxy]pent-2-enoate (Compound No.38): a solid with m.p. 53–55° C.

methyl 4-[5-(4-chloro-5-difluoromethoxy-1-methyl-(1H)-pyrazol-3-yl]-3-methoxybut-(E)-2-enoate (Compound No.39)

methyl 4-[5-(4-chloro-5-difluoromethoxy-1-methyl-(1H)-pyrazol-3-yl]pent-2-enoate (Compound No.40)

4-chloro-3-[4-chloro-2-fluoro-5-(4-methoxybut-2-ynyloxy) phenyl]-5-difluoromethoxy-1-methyl-(1H)-pyrazole (Compound No.41)

methyl 4-[4-chloro-2-fluoro-5-(5-isopropylidene-1,3-oxazolidine-2,4-dion-3-yl)phenyl]pent-2-enoate (Compound No.42).

EXAMPLE 6

Preparation of methyl 4-[2-chloro-4-fluoro-5-[(tetrahydro-3-oxo-1H-3H-[1,3,4]-thiadazole[3,4-a] pyridazin-1-ylydene)amino]phenoxy]pent-2-enoate (Compound No.43)

To a flask of 100 ml of capacity, by operating under a nitrogen atmosphere, a solution of 1.5 g of 4-[4-chloro-2-fluoro-5-(4-methoxycarbonyl-but-3-en-2-yloxy)phenyl]-1,2-tetramethylene-thio-semicarbazide (3.65 mmol) dissolved in 15 ml of methylene chloride and 0.77 ml of pyridine (9.48 mmol) are charged.

Then 0.3 ml is added dropwise of trichloromethyl chloroformate (2.48 mmol) dissolved in 3 ml of methylene chloride, and the resulting mixture is kept under stirring at room temperature during 16 hours.

The mixture is poured into water, the resulting aqueous mixture is extracted with methylene chloride, is thoroughly dried with sodium sulfate and is then concentrated under vacuum. The raw product is purified by silica gel chromatography yielding 0.9 g of a thick oil corresponding to the desired product.

EXAMPLE 7

Preparation of 8-[4-chloro-2-fluoro-5-(4-methoxycarbonyl-but-3-en-2-yloxy)phenyl]-1,6,8-triazabicyclo(4.3.0)nonane-7,9-dione(Compound No.44)

To a flask of 100 ml of capacity, under a nitrogen atmosphere, 1.25 g (3.2 mmol) of 4-[4-chloro-2-fluoro-5-(4-methoxycarbonyl-but-3-en-2-yl oxy)phenyl]-1,2-tetramethylene-semicarbazide dissolved in 20 ml of anhydrous toluene, 1.95 ml (14.1 mmol) of triethylamine and a tip of spatula of activated charcoal are charged. Then, 0.42 ml of trichloromethyl chloroformate (3.52 mmol) dissolved in 10 ml of toluene is added dropwise in a very slowly way and the resulting mixture is kept under stirring for 6 hours at room temperature and for 2 hours at 55° C. The resulting mixture is dropped to water, is extracted with ethyl ether, the organic phase is desiccated with sodium sulfate, and is then concentrated under vacuum. The resulting raw material is purified by silica gel chromatography, with 1.1 g being obtained of a product which is crystallised from a 1:1 mixture of exane:ethyl acetate. A yield is obtained of 0.8 g of a solid product with m.p. 113–114° C., corresponding to the desired product.

EXAMPLE 8

By operating analogously to as disclosed in Example 6, but starting from the corresponding thiosemicarbazide and trichloromethyl chloroformate, the following was obtained:

9-[4-chloro-2-fluoro-5-(4-methoxybut-2-ynyloxy) phenylimino]-8-thia-1,6-diazabicyclo-[4.3.0]nonan-7-one (Compound No.45).

By operating analogously to as disclosed in Example 7 but starting from the corresponding semicarbazide and trichloromethyl chloroformate, the following was obtained:

8-[4-chloro-2-fluoro-5-(4-methoxybut-2-ynyloxy)-phenyl]-1,6,8-triazabicyclo[4.3.0]-nonane-7,9-dione (Compound No.46); a solid with m.p. 114–116° C.

EXAMPLE 9

Preparation of N-[4-chloro-2-fluoro-5-(2-methoxy-3-methoxycarbonyl-(E)-prop-2-enyloxy)phenyl-$N^1$, $N^1$-diethylenoxy-1,2-cyclohex-1-ene-dicarboxamide (Compound No. 47)

To a small reaction flask of 100 ml of capacity, 1 g (2.36 mmol) of methyl 4-[2-chloro-5-(cyclohex-1-ene-1,2-dicarboximido)-4-fluorophenoxy]-3-methoxy-but-(E)-2-enoate (Compound No.3) dissolved in 20 ml of toluene and 0.27 ml (3.1 mmol) of morpholine are added. The reaction mixture is kept under stirring at room temperature during 48 hours. The resulting reaction mixture is concentrated under vacuum, the residue is diluted with ethyl ether and the resulting solid precipitate is filtered off and crystallised from ethyl acetate. A yield is obtained of 0.35 g of desired product (m.p. 125–127° C.)

EXAMPLE 10

Determination of post-emergence herbicidal activity

The herbicidal activity of Compound Nos. 1, 3, 7, 17 and 21 against weeds and crops was evaluated in post-emergency treatment, as compared to the activity displayed by ethyl 4-[5-(cyclohex-1-ene-1,2-dicarboximido)-2,4-dichlorophenoxy]crotonate, (CR1), Compound No.168 of U.S. Pat. No. 4,536,209, and N-[4-chloro-2-fluoro-5-(but-3-yn-2-yloxy)phenyl]-cyclohex-1-ene-1,2-dicarboximide, (RC2), corresponding to the Compound No. 4 of U.S. Pat. No. 4,736,068.

The evaluation tests for each product were carried out according to the following operating modalities.

Inside small pots containing sandy ground (10 cm of diameter, 10 cm high) the following weeds and crops were sown (10 pots per each species):

weeds: *Abutilon theofrasti* (AT), *Chenopodium album* (CA), *Convolvulus sepium* (CS), *Ipomea purpurea* (IP), *Portulaca oleracea* (PO), *Solanum nigrum* (SN);

crops: *Zea mays* (M), *Glycine max* (S)

To each pot a suitable amount of water for a good germination of the seeds was added.

The pots were subdivided into two groups, each containing 5 pots per each weed or valuable species.

After 15 days of sowing, i.e., when the seedlings (according to the species), were 10–15 cm tall, the first group of pots were treated with a water-acetone dispersion containing the product to be tested at the desired concentration, 10% (by vol.) acetone and 0.5% Tween 20.

The second group of pots were only treated with a water-acetone solution containing 10% of acetone by volume and 0.5% Tween 20, and were used as comparison standard (control).

All pots were uniformly watered every second day and were kept in a conditioned environment under the following condition:

temperature: 24° C.
relative air humidity: 60%
lighting period: 16 hours
light intensity: 10000 lux The herbicidal activity was evaluated 15 days after the treatment and was expressed according to a scale of values from 0 to 100, referred to the percent damage observed on treated plants as compared to non-treated (control) plants.

According to such a scale:
0=no herbicidal effects;
100=death of treated plant.

The results of the evaluations are reported in following Table 1.

We claim:

1. An arylheterocycles compound having the general formula (I):

(I)

[Structure: benzene ring with F, E, Y, and Z—Q substituents]

wherein:

Y represents a hydrogen atom, a chlorine, fluorine, or bromine atom; a linear or branched $C_1-C_4$ alkyl or haloalkyl radical, a linear or branched $C_1-C_4$ alkoxy or haloalkoxy radical; a linear or branched $C_1-C_4$ alkylthio or haloalkylthio radical;

Z represents an oxygen atom;

Q represents one of the following radicals:

$$Q_1: -\underset{R_2}{\overset{R_1}{\underset{|}{\overset{|}{C}}}} -C \equiv C - \underset{R_4}{\overset{R_3}{\underset{|}{\overset{|}{C}}}} -Z_1-(CO)_p-R;$$

$$Q_3: -\underset{R_2}{\overset{R_1}{\underset{|}{\overset{|}{C}}}} -CX_1=CX_2-COOR;$$

$$Q_4: -\underset{R_2}{\overset{R_1}{\underset{|}{\overset{|}{C}}}} -CX_1=CX_2-CONR_5R_6;$$

$$Q_5: -\underset{R_2}{\overset{R_1}{\underset{|}{\overset{|}{C}}}} -CX_1=CX_2-CX_3=C\overset{X_4}{\underset{COOR}{\diagdown}};$$

wherein:

R represents a hydrogen atom; or a linear or branched $C_1-C_6$ alkyl or haloalkyl radical;

TABLE 1

POST-EMERGENCE HERBICIDAL ACTIVITY AT DOSAGE RATES OF 50–15 G/HA

| COMPOUND | DOSAGE RATES (G/HA) | TESTED SPECIES | | | | | | | |
|---|---|---|---|---|---|---|---|---|---|
| | | AT | CA | CS | IP | PO | SN | M | S |
| 1 | 50 | 100 | 100 | 100 | 100 | 100 | 100 | 10 | 32 |
| | 15 | 100 | 100 | 100 | 100 | 100 | 100 | 4 | 14 |
| 3 | 50 | 100 | 100 | 100 | 100 | 100 | 100 | 4 | 10 |
| | 15 | 100 | 100 | 40 | 100 | 100 | 100 | 2 | 4 |
| 7 | 50 | 100 | 100 | 100 | 100 | 100 | 100 | 4 | 10 |
| | 15 | 100 | 100 | 100 | 100 | 100 | 100 | 2 | 5 |
| 17 | 50 | 100 | 100 | 100 | 100 | 100 | 60 | 10 | 20 |
| | 15 | 94 | 100 | 100 | 80 | 100 | 30 | 4 | 12 |
| 21 | 50 | 100 | 100 | 100 | 100 | 100 | 100 | 4 | 50 |
| | 15 | 100 | 100 | 40 | 100 | 100 | 100 | 2 | 20 |
| RC1 | 50 | 40 | 45 | 40 | 20 | 4 | 35 | 2 | 25 |
| | 15 | 30 | 25 | 20 | 10 | 0 | 4 | 0 | 20 |
| RC2 | 50 | 100 | 100 | 100 | 100 | 100 | 100 | 50 | 100 |
| | 15 | 100 | 100 | 100 | 100 | 100 | 30 | 65 | 65 |

$R_1$, $R_3$ and $R_4$, each independently, represent a hydrogen atom or methyl;

$R_2$ is hydrogen;

$R_5$ and $R_6$, each independently, represent a hydrogen atom; a linear or branched $C_1$–$C_4$ alkyl radical; or, together, they represent a $C_2$–$C_5$ alkylene chain, or a $C_2$–$C_5$ oxyalkylene chain;

$X_1$ represents hydrogen or $C_1$–$C_4$ alkoxy, $X_2$, $X_3$ and $X_4$, each represent a hydrogen atom;

$Z_1$ represents an oxygen atom;

p represents 0;

E represents the following heterocyclic radical $E_1$:

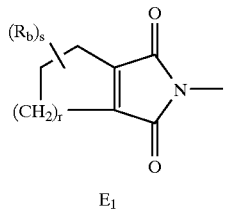

wherein:

$R_b$ represents a linear or branched $C_1$–$C_3$ alkyl radical;

r represents 1 or 2; and s represents an integer within the range of from 0 and 2 inclusive.

2. A herbicide comprising an arylheterocycle compound having the general formula (I):

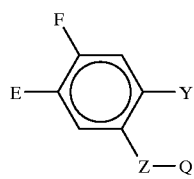

(I)

wherein:

Y represents a hydrogen atom, a chlorine, fluorine, or bromine atom; a linear or branched $C_1$–$C_4$ alkyl or haloalkyl radical, a linear or branched $C_1$–$C_4$ alkoxy or haloalkoxy radical; a linear or branched $C_1$–$C_4$ alkylthio or haloalkylthio radical;

Z represents an oxygen atom;

Q represents one of the following radicals:

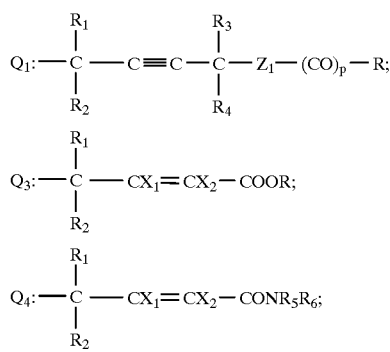

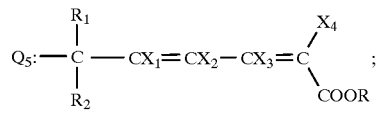

wherein:

R represents a hydrogen atom; or a linear or branched $C_1$–$C_6$ alkyl or haloalkyl radical;

$R_1$, $R_3$ and $R_4$, each independently, represent a hydrogen atom or methyl;

$R_2$ is hydrogen;

$R_5$ and $R_6$, each independently, represent a hydrogen atom; a linear or branched $C_1$–$C_4$ alkyl radical; or, together, they represent a $C_2$–$C_5$ alkylene chain, or a $C_2$–$C_5$ oxyalkylene chain;

$X_1$ represents hydrogen or $C_1$–$C_4$ alkoxy, $X_2$, $X_3$ and $X_4$, each represent a hydrogen atom;

$Z_1$ represents an oxygen atom;

p represents 0;

E represents the following heterocyclic radical $E_1$:

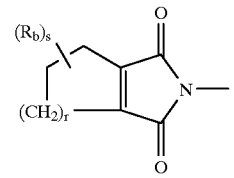

wherein:

$R_b$ represents a linear or branched $C_1$–$C_3$ alkyl radical;

r represents 1 or 2; and s represents an integer within the range of from 0 and 2 inclusive.

3. Process for preparing a arylheterocycle having the general formula (I) according to claim 1, which comprises reacting a phenol or a thiophenol having the general formula (II):

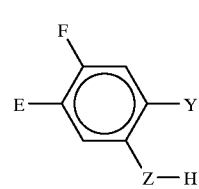

(II)

with a compound having the general formula (III):

Y represents a hydrogen atom, a chlorine, fluorine, or bromine atom; a linear or branched $C_1$–$C_4$ alkyl or haloalkyl radical, a linear or branched $C_1$–$C_4$ alkoxy or haloalkoxy radical; a linear or branched $C_1$–$C_4$ alkylthio or haloalkylthio radical;

Z represents an oxygen atom;

E represents the following heterocyclic radical $E_1$:

$$E_1$$

Q represents one of the following radicals:

$$Q_1: -\overset{R_1}{\underset{R_2}{C}}-C\equiv C-\overset{R_3}{\underset{R_4}{C}}-Z_1-(CO)_p-R;$$

$$Q_3: -\overset{R_1}{\underset{R_2}{C}}-CX_1=CX_2-COOR;$$

$$Q_4: -\overset{R_1}{\underset{R_2}{C}}-CX_1=CX_2-CONR_5R_6;$$

$$Q_5: -\overset{R_1}{\underset{R_2}{C}}-CX_1=CX_2-CX_3=\overset{X_4}{\underset{COOR}{C}};$$

wherein:
R represents a hydrogen atom; or a linear or branched $C_1-C_6$ alkyl or haloalkyl radical;
$R_1$, $R_3$ and R4, each independently, represent a hydrogen atom or methyl;
$R_2$ is hydrogen;
$R_5$ and $R_6$, each independently, represent a hydrogen atom; a linear or branched $C_1-C_4$ alkyl radical; or, together, they represent a $C_2-C_5$ alkylene chain, or a $C_2-C_5$ oxyalkylene chain;
$R_6$ represents a linear or branched $C_1-C_3$ alkyl radical;
r represents 1 or 2; and

X'—Q       (III)

in which X' represents a halogen atom or a R'SO$_2$O moiety in which R' represents a linear or branched $C_1-C_4$ alkyl or haloalkyl radical, or a phenyl radical, which may also be possibly substituted by linear or branched $C_1-C_3$ alkyl radicals, nitro groups, halogen atoms, in the presence of an inert organic solvent and in the presence of an either inorganic or organic base, at a temperature comprised within the range of from −10° C. to the boiling temperature of the solvent used.

4. A Herbicide according to claim 2, constituted by N-[4-chloro-2-fluoro-5-(4-methoxy-but-2-ynyloxy)phenyl] cyclohex-1-ene-1,2-dicarboximide.

5. A Herbicide according to claim 2, constituted by methyl 4-[2-chloro-5-(cyclohex-1-ene-1,2-dicarboximido)-4-fluorophenoxy]-3-methoxybut-(E)-2-enoate.

6. A Herbicide according to claim 2, constituted by N-[4-chloro-2-fluoro-5-(5-methoxypent-3-yn-2-yloxy) phenyl]-cyclohex-1-ene-1,2-dicarboximide.

7. A Herbicide according to claim 2, constituted by ethyl 4-[2-chloro-5-(cyclohex-1-ene-1,2-dicarboximido)-4-fluoro-phenoxy]crotonate.

8. A Herbicide according to claim 2, constituted by methyl 4-[2-chloro-5-(cyclohex-1-ene-1,2-dicarboximido)-4-fluorophenoxy]pent-2-enoate.

9. Process according to claim 3, in which the temperature is comprised within the range of from 0 to 100° C.

10. A Process according to claim 3, in which the inert organic solvent is selected from benzene, toluene, xylene, acetone, methyl ethyl ketone, methyl propyl ketone, ethyl acetate, dimethoxyethane, diisopropyl ether, tetrahydrofuran, dioxane, acetonitrile, N,N-dimethylformamide, N,N-dimethylacetamide, N-methylpyrrolidone, dimethyl sulfoxide.

11. A Process according to claim 3, in which the inorganic base is selected from sodium, potassium and calcium hydroxes and carbonates.

12. A Process according to claim 3, in which the is organic base is selected from triethylamine, pyridine, 4-dimethylamino pyridine, diazabicyclo-octane (DABCO), diazabicycloundecene (DBU).

13. A Process for preparing an arylheterocycles having the general formula (I) according to claim 1, in which E represents the $E_1$ moiety having the general formula (I-1):

(I-1)

wherein Y, Z, Q, $R_b$, s and r have the same meanings as disclosed above, which process consists in reacting an anhydride having the general formula (IV):

(IV)

wherein $R_b$, s, and r, have the same meanings as disclosed above, with an aniline having the general formula (V):

(V)

wherein Y, Z, and Q have the same meanings as defined above, either in the absence or in the presence of an inert organic solvent, at a temperature comprised within the range of from room temperature up to the boiling temperature of the possibly used solvent, possibly in the presence of a catalyst.

14. A Process according to claim 13, in which the reaction temperature is comprised within the range of from 60° C. to 200° C.

15. A Process according to claims 13 or 14, in which the inert organic solvents are benzene, toluene, xylene, chlorobenzene, acetic acid, diisopropyl ether, dimethoxyetane, tetrahydrofuran, dioxane.

16. A Process according to any of claim 13, in which the catalysts are mixture of nitrogenous organic bases with aliphatic carboxy acids.

17. A Process according to claim 16, in which the nitrogenous organic bases are triethylamine, piperidine, pyrrolidine and the aliphatic carboxy acids are acetic acid, propionic acid, butyric acid.

18. A composition having herbicidal activity containing one or more arylheterocycle compounds according to claim 2, in the presence of solid carriers, liquid diluents, surfactants or other active substances.

19. A composition having herbicidal activity according to claim 18, in which the concentration of active substance is within the range of from 1% to 90%.

20. A Method for controlling weeds in crop areas, comprising applying to said crop area the composition according to claim 18.

* * * * *